United States Patent [19]

Kanner et al.

[11] Patent Number: 5,392,790
[45] Date of Patent: Feb. 28, 1995

[54] INSTRUMENT FOR OBTAINING BORE TYPE TISSUE SAMPLING

[75] Inventors: Rowland W. Kanner; Richard M. Davis, both of Guntersville, Ala.

[73] Assignee: Ryder International Corporation, Arab, Ala.

[21] Appl. No.: 56,256

[22] Filed: Apr. 30, 1993

[51] Int. Cl.⁶ .............................................. A61B 10/00
[52] U.S. Cl. ................................................... 128/753
[58] Field of Search ........................ 128/749, 751–754; 606/167, 170

[56] References Cited

U.S. PATENT DOCUMENTS

| | | |
|---|---|---|
| 2,708,437 | 5/1955 | Hutchins . |
| 3,844,272 | 10/1974 | Banko . |
| 4,396,021 | 8/1983 | Baumgartner ............... 128/754 |
| 4,598,710 | 7/1986 | Kleinberg et al. ............ 128/751 |
| 4,766,907 | 8/1988 | de Groot et al. ............. 128/754 |
| 4,953,558 | 9/1990 | Akerfeldt ..................... 128/754 |
| 5,156,160 | 10/1992 | Bennett ........................ 128/754 |
| 5,172,701 | 12/1992 | Leigh ........................... 128/753 |
| 5,224,470 | 7/1993 | Schnepp-Pesch et al. .... 128/753 |

FOREIGN PATENT DOCUMENTS 728852 5/1980 U.S.S.R. .

*Primary Examiner*—Max Hindenburg
*Attorney, Agent, or Firm*—Trexler, Bushnell, Giangiorgi & Blackstone, Ltd.

[57] ABSTRACT

A tissue sampling instrument for aspirating sample tissue into a needle structure includes a suction chamber having first and second moveable chamber walls arranged to enlarge the volume of the chamber and reduce the pressure therein by movement of at least one of the first and second chamber walls. The needle structure has a lumen arranged in flow communication with the suction chamber to enable communication of the reduced pressure to the lumen in order to promote aspiration of sample tissue into a separate tissue entry aperture formed into the lumen. In one embodiment, the two moveable chamber walls are defined by a displaceable cylinder structure and piston structure moveable within the cylinder structure. The moveable cylinder and piston are formed within a separate housing. The suction action within the chamber is generated by a triggered advancement of the cylinder and cannula secured thereon relative to the piston and stylet so that the suction action is communicated to aspirate sample tissue into the cannula severed by the cutting advancement of the cannula carried on the cylinder. A variable stroke length of the cannula advancement is provided by a multiply-dimensioned stop structure.

24 Claims, 5 Drawing Sheets

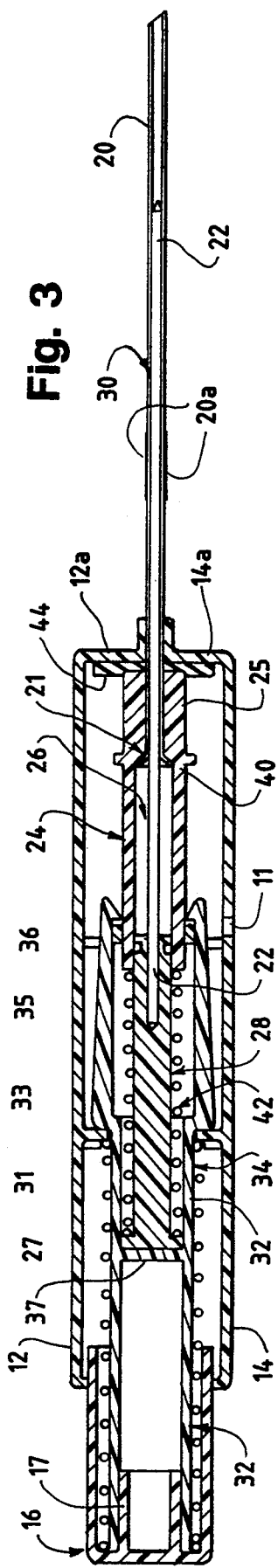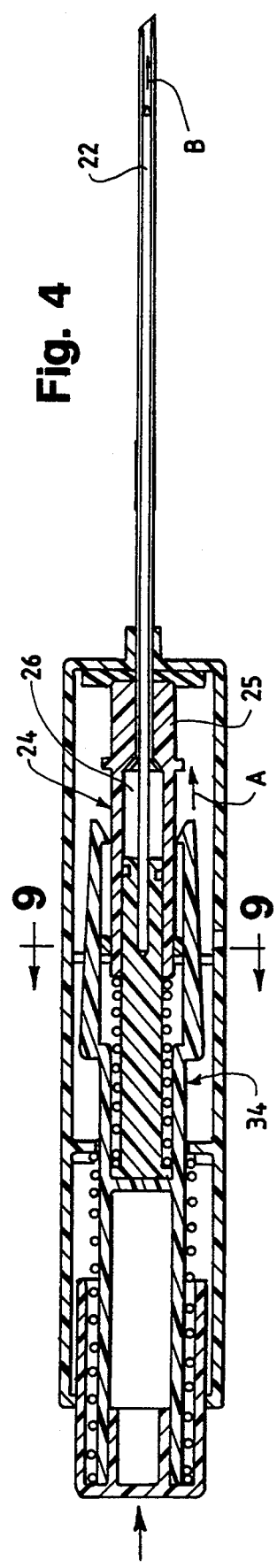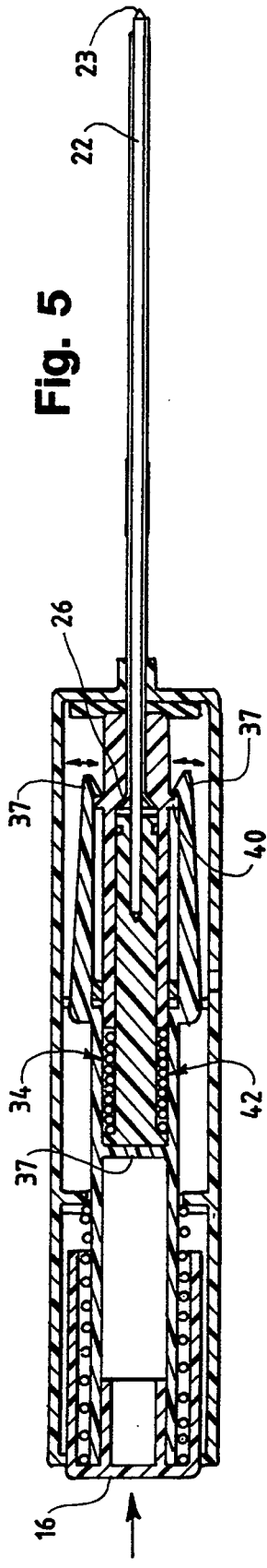

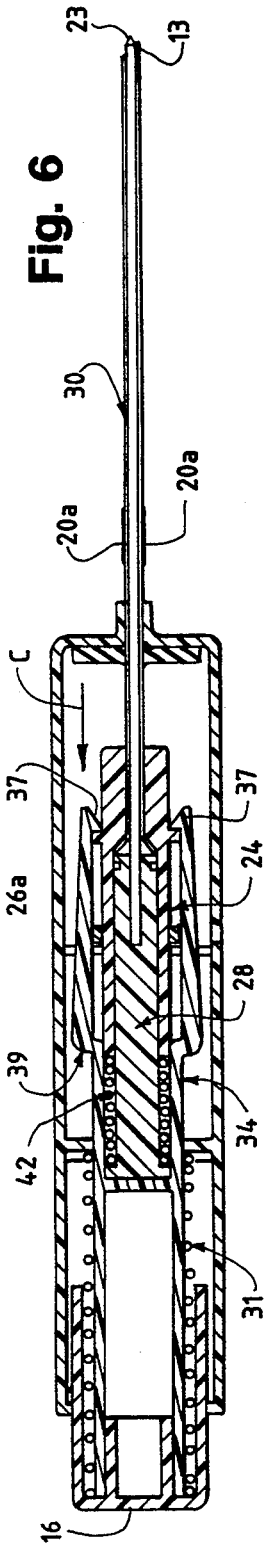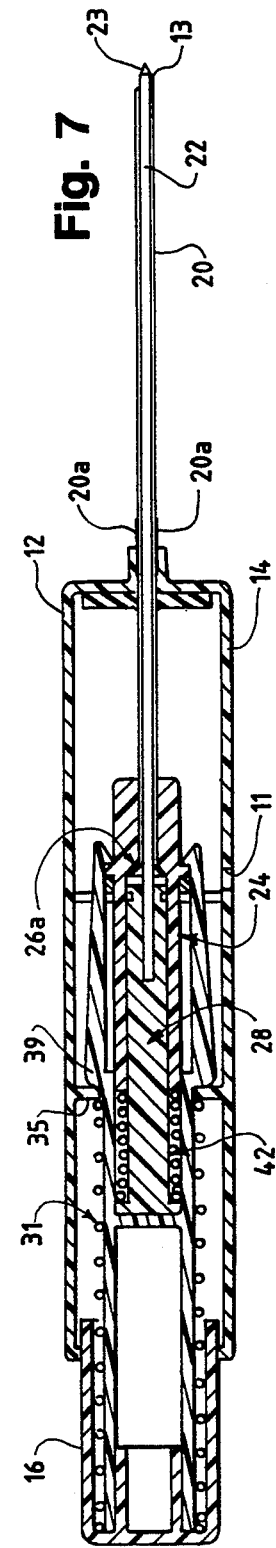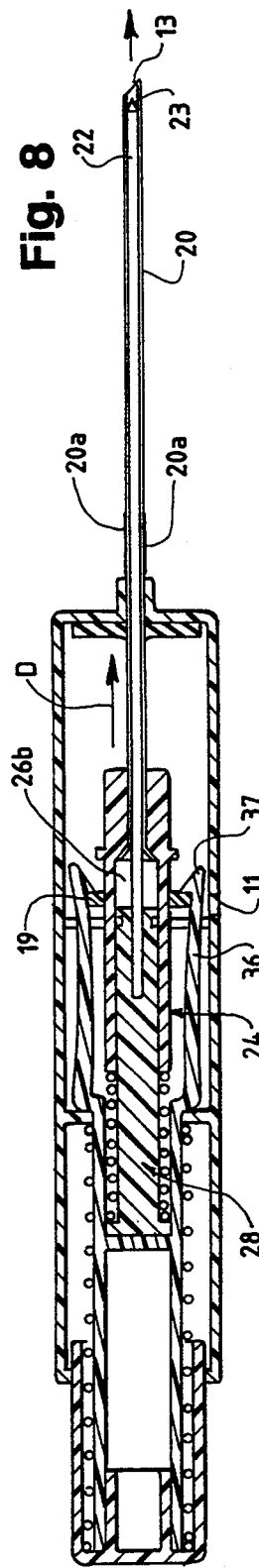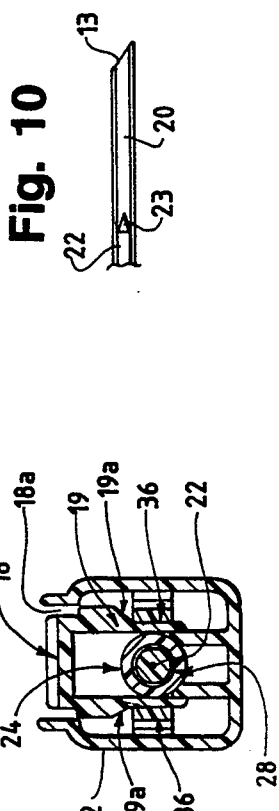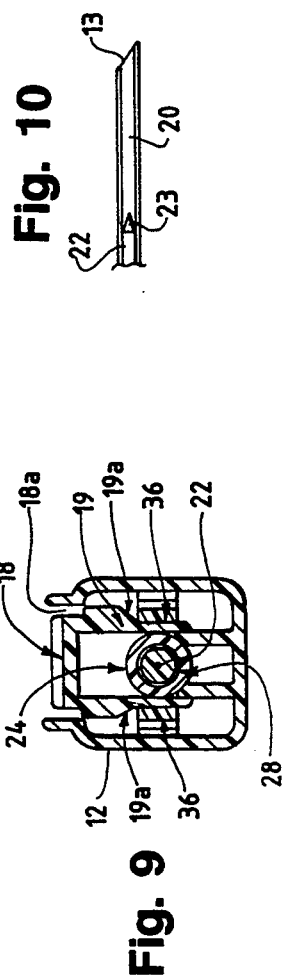

INSTRUMENT FOR OBTAINING BORE TYPE TISSUE SAMPLING

BACKGROUND OF THE INVENTION

The present invention relates to instruments for obtaining tissue samples, particularly for mammary biopsy procedures. More particularly, the invention relates to improved instruments for mechanically powered needle assemblies to sample the diagnostic tissue.

Syringe-type sampling instruments referred to as so-called Menghini needles incorporate an outer cylindrical body which is connected at one end to a hollow cannula needle through which a needle stylet is slidably supported on a piston inside the cylindrical body, as more fully described in U.S. Pat. No. 4,619,272. This patent describes operation of the piston and cylinder to create a suction chamber which draws tissue sample into the connected cylindrical cannula. The instrument described in this patent, however, requires manual operation of the piston.

Additional development of such syringe-type biopsy needle instruments is described U.S. Pat. No. 5,172,701. This patent describes a spring-driven piston in which the cylinder is formed by the housing itself so that the suction chamber is dependent on the housing dimension. This patent also describes instruments in which the spring is located within the suction chamber with consequent reduction in the volumetric ratio of the chamber expansion and suction action which can be developed for aspirating tissue sample into the cannula. These instruments also incorporate a complex one-way valve for venting the suction chamber.

These and other disadvantages are eliminated in improved tissue sampling instruments according to the present invention.

SUMMARY OF THE INVENTION

In accordance with the present invention, a tissue sampling instrument for aspirating sample tissue into a needle structure includes a suction chamber having first and second moveable chamber walls arranged to enlarge the volume of the chamber and reduce the pressure therein by movement of at least one of the first and second chamber walls. The needle structure has a lumen arranged in flow communication with the suction chamber to enable communication of the reduced pressure to the lumen in order to promote aspiration of sample tissue into a separate tissue entry aperture formed into the lumen.

In one embodiment, the two moveable chamber walls are defined by a displaceable cylinder structure and piston structure moveable within the cylinder structure. The moveable cylinder and piston are formed within a separate housing. Separate springs are provided for separate biasing and displacements of the cylinder and piston. In one embodiment, the suction action within the chamber is generated by a triggered advancement of the cylinder and cannula secured thereon relative to the piston and stylet so that the suction action is communicated to aspirate sample tissue into the cannula severed by the cutting advancement of the cannula carried on the cylinder. A variable stroke length of the cannula advancement is provided by a multiply-dimensioned stop structure.

BRIEF DESCRIPTION OF THE DRAWINGS

FIG. 3 is sectional view along a plane indicated by a line 3—3 in FIG. 1, looking downwardly;

FIGS. 4–7 are sectional views similar to FIG. 3, illustrating sequential motions in arming the needle drive structures of the instrument;

FIG. 8 is a sectional view similar to FIGS. 3–7, illustrating release of the needle drive structures;

FIG. 9 is sectional view along the plane indicated by line 9—9 in FIG. 4, illustrating a trigger mechanism for the needle drive structure;

FIG. 10 is a distal view of the stylet and the cannula;

DESCRIPTION OF THE ILLUSTRATED EMBODIMENTS

Figure 1:
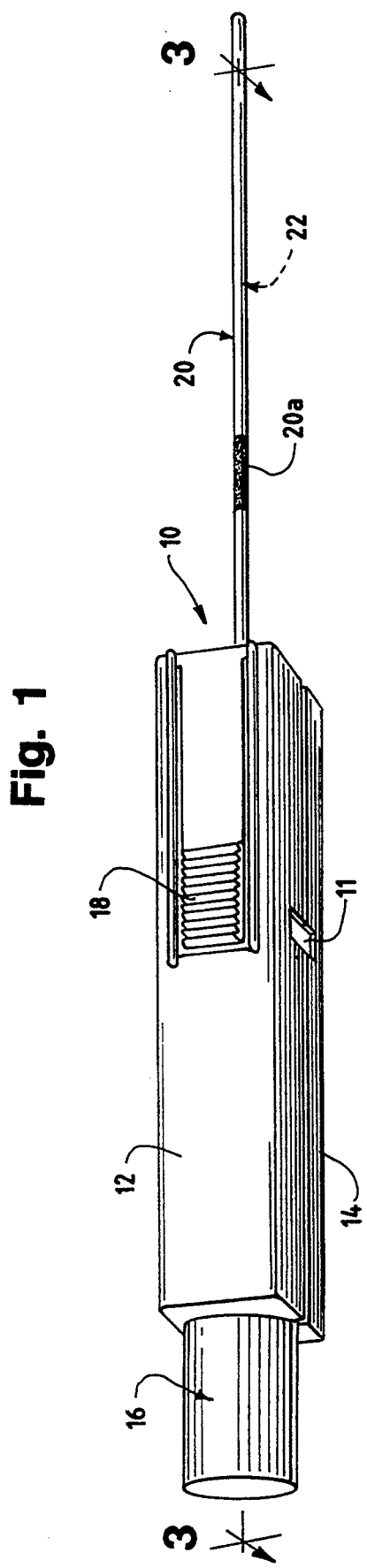
FIG. 1 is a perspective view of one embodiment of a tissue sampling instrument in accordance with the present invention.
Figure 2:
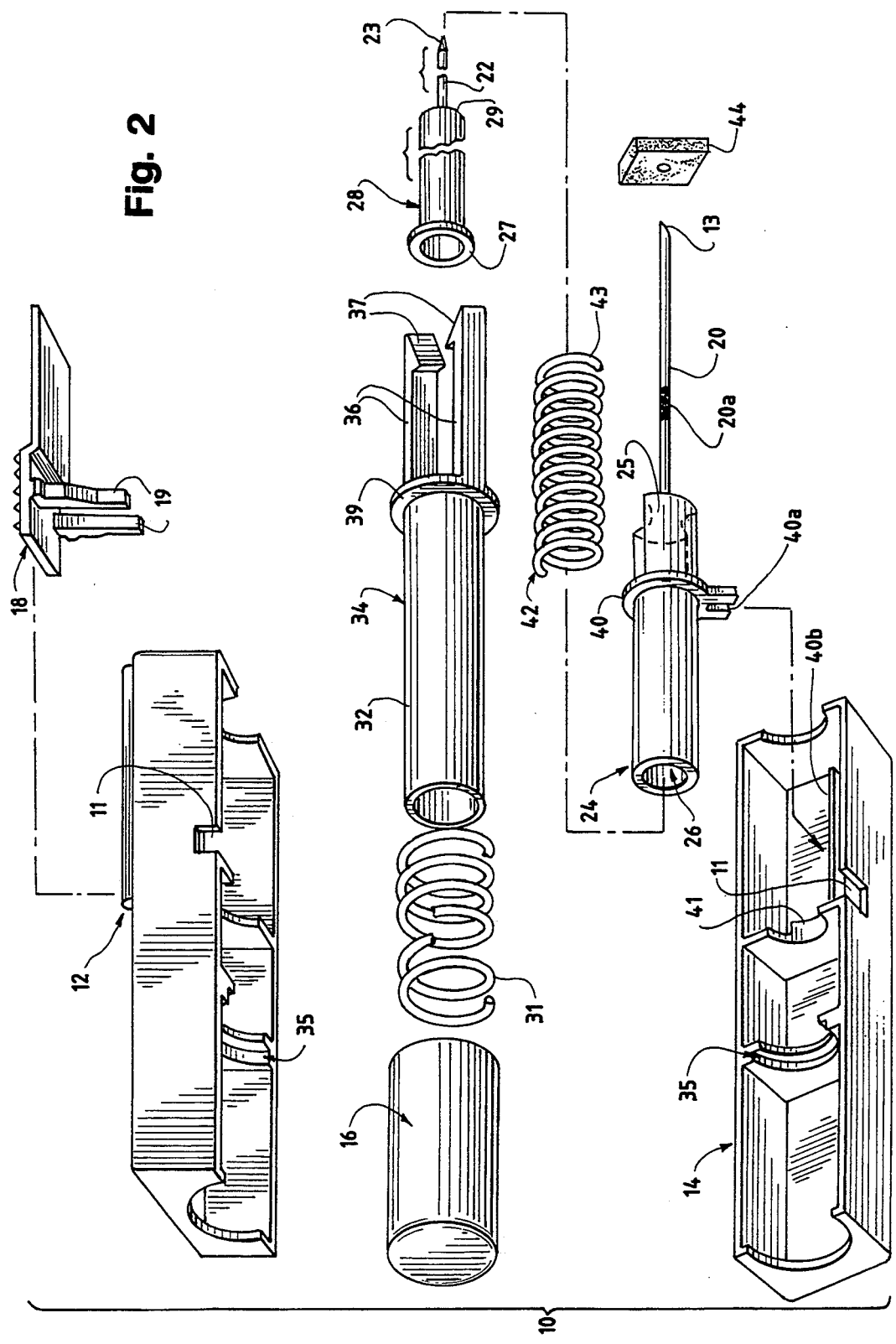
FIG. 2 is an exploded view of the instrument shown in FIG. 1.

Referring to FIGS. 1 and 2, one embodiment of a tissue sampling instrument in accordance with the present invention is designated generally by reference character 10. Instrument 10 has a longitudinally-split upper housing 12 and lower housing 14 from which a cocking or arming plunger button 16 projects rearwardly. An operating trigger button 18 is molded on the upper housing 12 for manual depression through a housing slot 18a as best shown in FIG. 9 and more fully described hereinafter.

The two-part needle structure of the instrument 10 has a cylindrical cannula 20 through which an inner stylet 22 is slidably displaceable. The cannula 20 projects from a movable cylinder structure 24 and as shown in FIG. 3, the rear opening 21 of the cylindrical cannula 20 opens through the cylinder head 25 into the cylinder bore 26. The stylet is preferably (but need not be) a solid rod which projects from a piston structure 28 reciprocable through the cylinder bore 26. The forward end of the piston structure 28 carries an externally mounted O-ring 29 to provide internal, pneumatic seal of the bore-chamber 26 to enable generation of reduced pressure therein which can be communicated through the annular clearance space 30 surrounding the stylet 22 within the cannula 20. The suction action of the communicated reduced pressure assists the extraction of the full-core tissue sample in operation as more fully described hereinafter with reference to FIGS. 11–14.

Referring again to FIGS. 1 and 2, the arming plunger button 16 has an internal hub 17 which is fixed to the rear cylindrical portion 32 of a sear or arming coupler generally designated by reference character 34. A return coil spring 31 surrounds the coupler cylinder 32 and bears at one end against the plunger button 16; the opposite spring end 33 is stationary and seats on an annular internal flange 35 of the housing 12, 14, through which the coupler cylinder 32 is axially displaceable. The expanded spring 31 biases the plunger, arming button 16 in position extended from the housing 12, 14. The forward portion of the arming coupler 34 has a pair of spaced, axially projecting coupler arms 36 with end barbs 37 which releasably latch and couple to the annular cylinder flange 40 radially extending from the moveable cylinder structure 24 during arming of the instrument 10 as later described with reference to FIG. 7.

Referring again to FIG. 3, the piston structure 28 is inserted within the coupler cylinder 32 and has an annular end flange 27 which seats on an internal wall 37 transversely extending across the cylinder 32 so that the piston structure 28 moves with the arming coupler 34. The piston flange 27 also seats one end of drive spring 42 which bears at its other end 43 on the annular rear end of the cylinder 24. The drive spring 42 thus urges the cylinder structure 24 forwardly so that in the unarmed condition of the expanded spring 42, the forward end of the cylinder head 25 is engaged against a cushion 44 seated on the internal end walls 12a, 14a of the housing 12, 14. The cylinder flange 40 has a guide slot 40a which axially slides on a guide rib 40b formed on the bottom housing 14. The cylinder 24 is slidably supported on a support flange 41 of the bottom housing 14.

FIGS. 3–7 illustrate the sequential positions in arming instrument 10 to prepare for tissue sampling operation. Arming of the instrument begins with manually depressing the plunger button 16 from the position shown in FIG. 3 through the positions in FIGS. 4 and 5 in which the return spring 31 is progressively compressed and the arming coupler 34 is forwardly advanced in the direction of arrow A in FIG. 4; the piston structure 28 is carried within the arming coupler 34 so that the stylet 22 is also advanced within the cannula 20 as indicated by arrow B in FIG. 4. During this advance phase of the arming operation, the cylinder structure 24 remains stationary since the cylinder head 25 abuts the cushion 44 and the advancing piston structure 28 reduces the volume of the cylinder bore chamber 26, as well as compressing the drive spring 42 against the stationary end of the cylinder 24.

When the advance phase of the instrument arming operation is completed with full depression of the button 16 as shown in FIG. 5, the latching barbs 37 ride over and latch against the cylinder flange 40 in snapping action, so that the resulting latch retains the compression of the drive spring 42 between the end of the cylinder 24 and the internal wall 37 of the coupler 34.

After the latching snap is felt by the user, the cylinder bore chamber 26 has been reduced to minimum volume as shown in FIG. 5 with completion of the advancing phase of the arming. Immediately following the arming advance phase, the reverse phase continues the arming operation with manually yielding withdrawal of the plunger button 16 driven by expansion of the return spring 31 so that the reverse phase progresses from the position shown in FIG. 5 to the position shown in FIG. 7. The arming reverse phase retracts the coupled cylinder structure 24 and piston structure 28 latched by the coupler arms 36 so that the drive spring 42 remains compressed as the cylinder 24, piston 28, and coupler 34 are retracted with the button 16 as indicated by arrow C in FIG. 6.

The rearward retraction of the cylinder 24 and piston 28 carries the stylet 22 and cannula 20 in the same rearward retraction into the housing 12, 14 without relative movement between the two needles so that the sharp stylet end 23 is slightly projecting from the sharp cannula end 13 and the cylinder bore chamber 26 remains at minimum volume.

When the instrument is fully armed as shown in FIG. 7, the reverse phase of the arming operation brings an annular flange at the base of the coupling arms 36 into abutment against the housing flange 35 which thus serves as a stop for the reverse phase retraction of the coupler 34 and the coupled cylinder structure 24 which in turn defines the fully expanded position of the return spring 31 and arming plunger button 16. A window 11 formed in the housing 14 (or 12) is positioned to enable visibility of the retracted, armed position of the cylinder flange 40 and cylinder 24, which provides an optical monitor of the armed or unarmed condition of the instrument 10, and readiness for tissue sampling operation. Additionally, a circumferential indicator band 20a on the cannula 20 can be longitudinally located to visibly underlap or abut the housing nose 12b, 14b, through which the cannula is slidably supported, when the instrument is armed as shown in FIG. 7, but the indicator band is spaced from the housing nose 12b, 14b when the cannula 20 has been advanced as shown in FIG. 3 after completion of tissue sampling operation when the instrument is unarmed.

Figure 11:
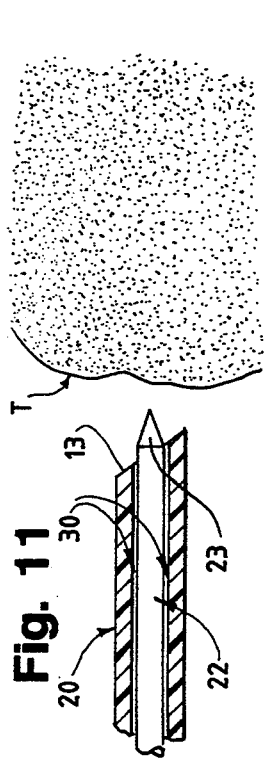
FIGS. 11 and 12 are fragmentary views diagrammatically showing a representative tissue sampling operation of the needle portions of the instrument, partially in section.

From the fully armed position of the instrument 10 shown in FIG. 7, the tissue sampling operation can begin as shown initially as in FIG. 11 in which the operator can direct the leading, stylet end 23 and cannula end 13 to the organ tissue T. (The sharpened stylet end 23 will assist pilot penetration [not shown] of the organ tissue T if the sample target lies at extended depth within the organ tissue T.) For simplicity of illustration, FIGS. 11 and 12 illustrate initial approach Of the stylet and cannula ends 23, 13 to the surface of the organ tissue T, for example, in obtaining mammary biopsy sample at shallow depth typically, approximately 2.5 centimeters from the stylet end 23.

From the armed position shown in FIG. 11, the tissue sampling operation can be triggered as illustrated with reference to FIGS. 8 and 9 by depressing the trigger button 18. The trigger button 18 has a pair of spaced, downwardly projecting trigger arms 19 which are respectively wedged between the exterior cylindrical surface of the cylinder structure 24 and the radially inner surface of the respective coupler arms 36. Depression of the trigger button 18 lowers the trigger arms 19 and cam portions 19a further wedge the coupler arms 36 radially outwardly, shown in FIG. 8 driving outward deflection of the barbs 37 which then release the latch of the retainer flange 40 and allows expansion of the drive spring 42 to forwardly propel the cylinder structure 24 and cannula 20 relative to the piston structure 28 and stylet 23 which remain fixed to the sear coupler structure 34 in the armed position shown in FIG. 7 under the bias of the expanded arming spring 31.

Figure 12:
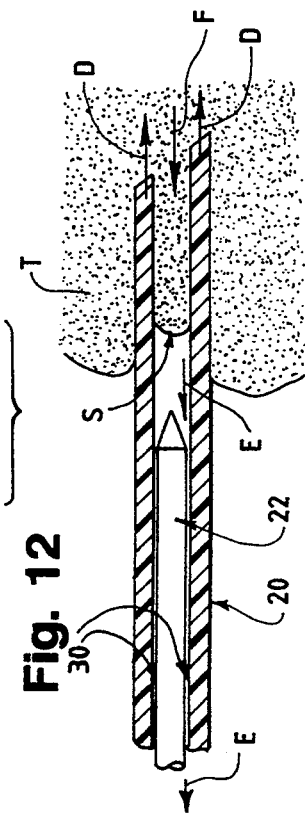
Figure 13:
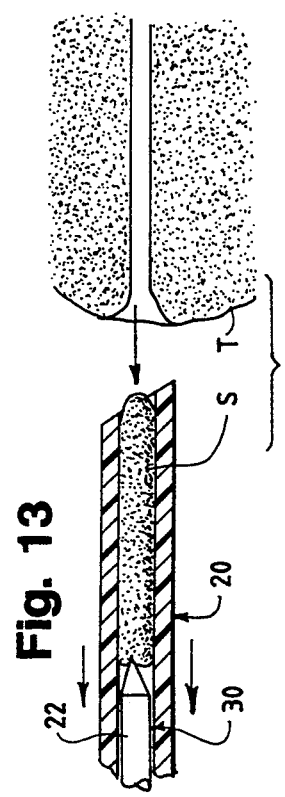
FIG. 13 is a view similar to FIGS. 11 and 12, illustrating withdrawal of the needle portions extracting sample tissue.
Figure 14:
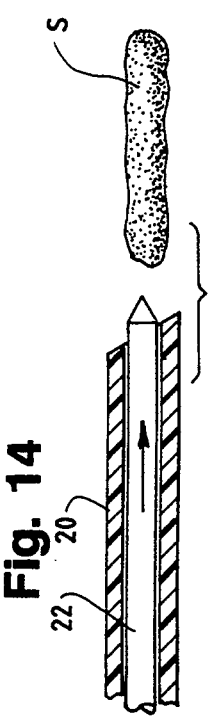
FIG. 14 is a view similar to FIG. 13, illustrating discharge of the extracted tissue sample from the needle portion.

As the cylinder structure 24 and cannula 20 are forwardly propelled relative to the stylet 22 as indicated by the arrow D shown in FIG. 8 corresponding FIG. 12, the displacement of the cylinder structure 24 relative to the piston structure 28 produces enlargement of the volume 26b within the cylinder bore chamber 26 and the inversely reduced pressure within the chamber 26 is communicated through the annular clearance space 30 which creates a rearward suction action therein as indicated by arrows E in FIG. 12. The induced suction action E promotes aspiration of a target tissue sample S core rearwardly as indicated by directional arrow F through the bore of the cannula 20 at the same time that the core sample S is severed from the surrounding tissue T by the forward advance of the sharp cannula end 13 as indicated by arrows D. When the full advance stroke is completed as shown in FIG. 3 which sequentially follows FIG. 8, the cushion stop 44 absorbs the impact of the cylinder head 25 and in this position the cylinder bore chamber 26 has expanded to its maximum volume; as the cannula 20 reaches maximum displacement relative to the stylet 22 as shown in FIG. 10 corresponding to FIG. 3, the maximum length of the severed and aspirated core sample S is drawn into the cannula 20 ahead of the relatively stationary stylet 22. Thereafter, the operator retracts the entire instrument 10 to withdraw the cannula 20 from the organ tissue T and the reduced pressure within the annular clearance 30 promotes the retention of the severed core sample S with the retracted cannula 20. Subsequently, the core tissue sample S can be discharged from the cannula 20 by the relative advance of the stylet 22 as shown in FIG. 14 as the instrument is rearmed in the advance phase between the positions shown in FIGS. 3-5.

Figure 15:
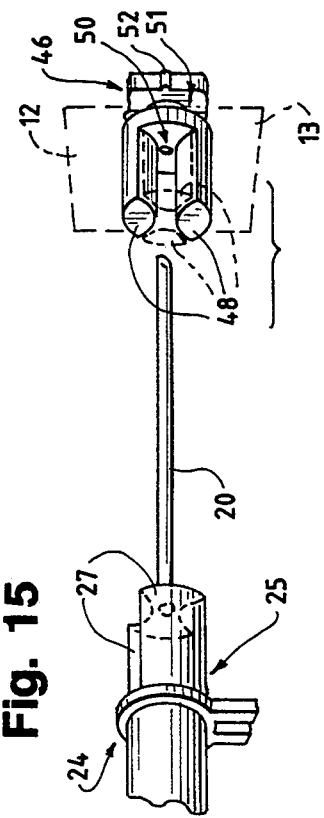
FIGS. 15, 16 and 17 are perspective, fragmentary views illustrating modification of the instrument in FIGS. 1 and 2 incorporating a variable stop structure to enable changing the length of needle displacement in tissue sampling operation of the instrument.
Figure 16:
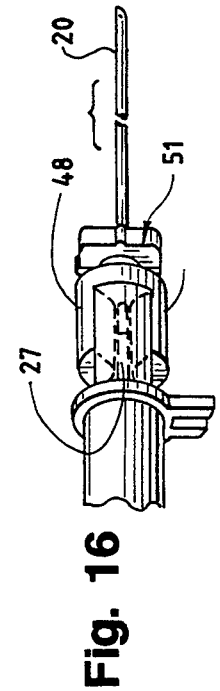
Figure 17:
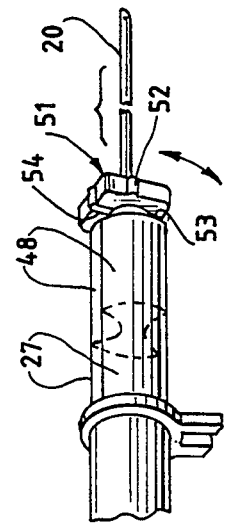

Referring to FIGS. 15-17, the cushion 44 can be replaced by a manually variable stop member generally designated by reference character 46. In the illustrated embodiment, the variable stop member 46 is a molded elastomeric in which two rearwardly projecting axial lobes 48 have a generally quarter-round configuration and are arranged in radially opposing alignment separated with central clearance for the cannula and stylet. Recess flutes 50 are radially arranged in alternation with the lobes 48. The flutes 50 can accept the axially projecting lobes 27 of the cylinder head 25 allowing a full advance stroke, for example of 2.5 centimeters displacement of the cannula 20 in the tissue sampling operating displacement thereof. Alternatively, the variable stop 46 can be manually rotated by the integral grip portion 51 which is accessible on the forward exterior of the housing 12, 14 as shown in FIG. 15, so that the stop lobes 48 are rotated by 90 degrees into the approaching path for abutting alignment with the cylinder head lobes 27. The abutment results in an abbreviated tissue sampling stroke, for example of approximately 1.3 centimeters displacement of the cannula 20, as governed by the depth of the target tissue sample and the desired length of the sample core to be extracted. The grip portion 51 of the variable stop member 46 has a generally square configuration provided with differential indicia 52 formed on one or both of adjacent quarter sides of the grip 51 to indicate the selective, quarter-turn orientations of the stop lobes 48 and resulting stroke length of the tissue sampling instrument operation. Additionally, indexing grooves 53 can be molded into the inner surface of the grip portion 51 for receiving a raised rib (not shown) on the outer surface of the housing 12, 14 in order to releasably retain the selective rotational position of the stop lobes 48.

While particular embodiments of the tissue sampling instrument have been described herein, it will be obvious to those skilled in the art that changes and modifications in various aspects may be made without departing from the broad scope of the invention. Consequently, the scope of the invention is not limited by any particular embodiment but is define by the appended claims and the equivalents thereof.

The invention claimed is:

1. A tissue sampling instrument for aspirating sample tissue into a needle structure, said instrument comprising: a suction chamber including at least first and second separately movable chamber walls arranged to enlarge volume of said chamber and reduce pressure therein by movement of at least one of said first and second chamber walls; and a needle structure having a lumen therein arranged in flow communication with said chamber to enable communication of said reduced pressure to said lumen and to promote aspiration of sample tissue into a tissue entry aperture formed in the lumen, during tissue sampling operation of said instrument.

2. An instrument according to claim 1, wherein said suction chamber is movably mounted within a separate housing structure.

3. An instrument according to claim 1, further comprising a first spring means for biasing said first chamber wall at a first, enlarged volume of said suction chamber, and second spring means for biasing said second chamber wall at said first, enlarged suction chamber volume.

4. An instrument according to claim 1, wherein said first and second chamber walls are opposingly arranged and biased toward opposing directions by said respective first and second spring means.

5. An instrument according to claim 3, wherein said first and second spring means are mounted external to said suction chamber.

6. An instrument according to claim 5, wherein said first spring means and said second spring means are arranged for coupled energization defining arming of said instrument for said tissue sampling operation.

7. An instrument according to claim 6, wherein said second spring means drives said movement of said second chamber wall and said volume enlargement of said suction chamber.

8. An instrument according to claim 1, wherein said first and second chamber walls form respective portions of a piston structure and a cylinder structure movable therein which define said suction chamber therebetween.

9. An instrument according to claim 8, wherein movement of said second chamber wall and said cylinder structure are driven by spring means.

10. An instrument according to claim 1, further comprising coupling means for coupling movement of said first and second chamber walls.

11. An instrument according to claim 8, wherein said needle structure includes a cylindrical cannula mounted and moveable on said cylinder structure and having a cylindrical bore defining said lumen.

12. A tissue sampling instrument for aspirating sample tissue into a needle structure, said instrument comprising a moveable cylinder structure and piston structure moveable within the cylinder structure to form a variable volume suction chamber within the cylinder structure which is expandable to generate reduced pressure therein; and a needle structure having a lumen therein arranged in flow communication with said suction chamber to enable communication of said reduced pressure to said lumen and to promote aspiration of sample tissue into a tissue entry aperture opening into the lumen, during tissue sampling operation of the instrument.

13. An instrument according to claim 12, wherein said needle structure includes a cylindrical cannula having said lumen therein through which a stylet is relatively translated axially, wherein said cannula and stylet are respectively secured to one of said cylinder structure and piston structure.

14. An instrument according to claim 12, further comprising cylinder spring means for driving motion of said cylinder structure and a cylindrical cannula secured thereon and including said lumen therein.

15. A tissue sampling instrument according to claim 14, comprising an arming spring means for moving said piston structure and to said cylinder structure coupled thereto.

16. An instrument according to claim 13, further comprising coupling means for coupling movement of said cylinder structure and piston structure in order to arm said instrument.

17. An instrument according to claim 16, wherein said coupling means comprises a carriage member on which said piston structure is secured for movement therewith, said carriage means and said cylinder structure including latch members cooperable to couple said carriage means and cylinder structure.

18. An instrument according to claim 17, further comprising release means for disengagement of said cooperable latch members.

19. An instrument according to claim 18, wherein said release means comprises a cam member selectively movable to displace at least one of said respective latch members in said disengagement.

20. An instrument according to claim 17, further comprising a cylinder spring compressible between said piston structure and cylinder structure for driving motion of said cylinder structure and a cylindrical cannula secured thereon and including said lumen therein, said coupling of said piston structure and cylinder structure maintaining compression of said cylinder spring, and an arming spring means for moving said coupled piston structure and cylinder structure to a release position thereof at which a release member is selectively displaceable to disengage said respective latch members enabling expansion of said cylinder spring for said driven motion of said cylinder structure and cannula relative to said piston structure and stylet in said tissue sampling operation.

21. An instrument according to claim 12, further comprising variable-stop means for selectively adjusting length of displacement of said needle structure secured to one of said movable cylinder structure and piston structure.

22. An instrument according to claim 12, wherein said piston structure and cylinder structure are arranged for relative movement to enable a two-phase arming operation including sequential forward movement of said piston structure relative to said cylinder structure followed by coupled movement of said piston structure and cylinder structure in reversed direction relative to said forward movement; and, thereafter forward movement of said cylinder structure relative to said piston structure in tissue sampling operation of said instrument.

23. A tissue sampling instrument comprising a housing within which is movable a needle structure having a tissue entry aperture therein, said needle structure being mounted on a movable carriage structure to enable thrusting said needle structure in a tissue sampling displacement thereof relative to said housing, and a variable-stop means for selectively adjusting the length of said displacement of said needle structure relative to said housing.

24. An instrument according to claim 23, wherein said variable-stop means comprises a plurality of differentially dimensioned stop members alternatively oriented for separate impact by said carriage structure in selectively different displacements thereof governed by said stop member dimensions.

* * * * *